(12) United States Patent
Sanson et al.

(10) Patent No.: US 7,851,440 B2
(45) Date of Patent: Dec. 14, 2010

(54) PEPTIDES WITH AFFINITY FOR A PHOSPHOLIPID AND USES

(75) Inventors: Alain Sanson, Gometz le Chatel (FR); Francoise Ochsenbein, Gif sur Yvette (FR)

(73) Assignees: Commissariat a l'Energie Atomique, Paris (FR); Universite Pierre et Marie Curie (Paris VI), Paris (FR)

( * ) Notice: Subject to any disclaimer, the term of this patent is extended or adjusted under 35 U.S.C. 154(b) by 887 days.

(21) Appl. No.: 10/518,383

(22) PCT Filed: Jun. 30, 2003

(86) PCT No.: PCT/FR03/02025
§ 371 (c)(1), (2), (4) Date: Dec. 29, 2004

(87) PCT Pub. No.: WO2004/003015
PCT Pub. Date: Jan. 8, 2004

(65) Prior Publication Data
US 2006/0148689 A1    Jul. 6, 2006

(30) Foreign Application Priority Data
Jul. 1, 2002    (FR) .................................. 02 08202

(51) Int. Cl.
*A61K 38/16* (2006.01)
(52) U.S. Cl. ........................................ 514/12; 530/324
(58) Field of Classification Search .................. None
See application file for complete search history.

(56) References Cited

U.S. PATENT DOCUMENTS
2002/0044941 A1 *    4/2002    Rosen et al. ............. 424/184.1

FOREIGN PATENT DOCUMENTS
| EP | 293 567 | 12/1988 |
| WO | 92/19279 | 11/1992 |
| WO | 00/10673 | 3/2000 |
| WO | 00/20453 | 4/2000 |

OTHER PUBLICATIONS

Pierre Montaville, et al., "A new consensus sequence for phosphatidylserine recognition by annexins", The Journal of Biological Chemistry, vol. 277, No. 27, pp. 24684-24693 Jul. 5, 2002.

Carol L. Sable, et al., "Cloning and functional activity of a novel truncated formed of annexin IV in mouse macrophages", Biochemical and Biophysical Research Communications, vol. 258, No. 1, pp. 162-167 1999.

Shuang Liu, et al., "99mTc labeling of highly potent small peptides", Bioconjugate Chem., vol. 8, No. 5, pp. 621-636 1997.

Kanthi P. Pulukkody, et al., "Synthesis of charged and uncharged complexes of gadolinium and yttrium with cyclic polyazaphosphinic acid ligands for in vivo applications", J. Chem. Soc. Perkin. Trans., vol. 2, pp. 605-620 1993.

* cited by examiner

*Primary Examiner*—Anish Gupta
(74) *Attorney, Agent, or Firm*—Oblon, Spivak, McClelland, Maier & Neustadt, L.L.P.

(57) ABSTRACT

The present invention relates to a peptide for the specific recognition of lipid vectors. The peptide of the invention comprises the peptide sequence (I; SEQ ID NO: 15) below:

$$J^1-J^2-J^3-J^4-J^5-J^6-Z^7-U^8-J^9-J^{10}-U^{11}-Arg-J^{13}-J^{14}-$$
$$U^{15}-Lys-Gly-X^{18}-Gly-Thr-J^{21}-Glu-J^{23}-J^{24}-U^{25}-J^{26}-$$
$$J^{27}-J^{28}-U^{29}-J^{30}-J^{31}-Arg-J^{33}-J^{34}-J^{35}-J^{36}-B^{37}-J^{38}-$$
$$J^{39}-U^{40}-J^{41}-J^{42}-J^{43}-U^{44}-J^{45}-J^{46}-J^{47}-J^{48}-J^{49}-Arg-$$
$$J^{51}-U^{52}-J^{53}-J^{54}-Asp-U^{56}-Lys-Ser-Z^{59}-Leu-J^{61}-J^{62}-$$
$$J^{63}-J^{64}-Z^{65}-J^{66}-J^{67}-U^{68}-J^{69}-J^{70}-J^{71}-U^{72}-J^{73}-J^{74}-$$
$$J^{75}$$

in which the amino acids J are chosen, independently of one another, from essential amino acids, or derivatives thereof, such that at least 50% of them are polar residues chosen from Arg, Asn, Asp, Cys, Gln, Glu, Gly, His, Lys, Orn, Pro, Ser, Thr and Tyr; the amino acids U are chosen, independently of one another, from Ala, Cys, Gly, Ile, Leu, Met, Phe, Trp, Tyr and Val; the amino acid $X^{18}$ is chosen, independently of the other amino acids of the sequence, from Ala, Asn, Cys, Gln, Gly, His, Ile, Leu, Met, Phe, Ser, Thr, Trp, Tyr and Val; the amino acid $B^{37}$ is chosen, independently of the other amino acids of the sequence, from Arg, Ala, Cys, Gly, Ile, Leu, Met, Phe, Trp, Tyr and Val; the amino acid $Z^7$ is chosen, independently of the other amino acids of the sequence, from Asp and Gly; the amino acids $Z^{59}$ and $Z^{65}$ are chosen from Glu, Asp, Lys or Arg; and the superscripts of the residues J, Z, U, X and B represent the position of these amino acids in said sequence.

61 Claims, 3 Drawing Sheets

AFIM-F

A5-F

H1

AFIM-F  H2  A5-F

```
                        SEQUENCE LISTING

<160> NUMBER OF SEQ ID NOS: 20

<210> SEQ ID NO 1
  <211> LENGTH: 75
  <212> TYPE: PRT
  <213> ORGANISM: Artificial Sequence
  <220> FEATURE:
  <223> OTHER INFORMATION: Synthetic Peptide; sequence derived from human
        annexin

<400> SEQUENCE: 1

Gly Phe Asp Glu Arg Ala Asp Val Glu Thr Leu Arg Lys Ala Met Lys
  1               5                   10                  15

Gly Leu Gly Thr Asp Glu Glu Ser Ile Leu Thr Leu Leu Thr Ser Arg
              20                  25                  30

Ser Asn Ala Gln Arg Gln Glu Ile Ser Ala Ala Tyr Lys Thr Leu Phe
          35                  40                  45

Gly Arg Asp Leu Leu Asp Asp Leu Lys Ser Glu Leu Thr Gly Lys Phe
      50                  55                  60

Glu Lys Leu Val Val Ala Leu Leu Lys Pro Ser
  65                  70                  75

<210> SEQ ID NO 2
  <211> LENGTH: 75
  <212> TYPE: PRT
  <213> ORGANISM: Artificial Sequence
  <220> FEATURE:
  <223> OTHER INFORMATION: Synthetic Peptide; sequence derived from human
        annexin

<400> SEQUENCE: 2

Asn Phe Asp Ala Glu Arg Asp Ala Leu Asn Ile Arg Lys Ala Ile Lys
  1               5                   10                  15

Gly Met Gly Val Asp Glu Asp Thr Ile Val Asn Ile Leu Thr Asn Arg
              20                  25                  30

Ser Asn Ala Gln Arg Gln Asp Ile Ala Phe Ala Tyr Gln Arg Arg Thr
          35                  40                  45

Lys Arg Glu Leu Ala Ser Asp Leu Lys Ser Glu Leu Ser Gly His Leu
      50                  55                  60

Glu Arg Val Ile Leu Gly Leu Leu Lys Thr Ser
  65                  70                  75

<210> SEQ ID NO 3
  <211> LENGTH: 75
  <212> TYPE: PRT
  <213> ORGANISM: Artificial Sequence
  <220> FEATURE:
  <223> OTHER INFORMATION: Synthetic Peptide; sequence derived from human
        annexin

<400> SEQUENCE: 3

Asp Phe Ser Pro Ser Val Asp Ala Glu Ala Ile Arg Lys Ala Ile Lys
  1               5                   10                  15

Gly Ile Gly Thr Asp Glu Asp Met Leu Ile Ser Ile Leu Thr Glu Arg
              20                  25                  30
```

```
Ser Asn Ala Gln Arg Gln Leu Ile Val Lys Glu Tyr Gln Ala Ala Tyr
        35                  40                  45

Gly Arg Glu Leu Lys Asp Asp Leu Lys Ser Glu Leu Ser Gly His Phe
 50                  55                  60

Glu Arg Leu Met Val Ala Leu Val Thr Pro Ser
 65                  70                  75

<210> SEQ ID NO 4
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 4

Gly Phe Asn Ala Met Glu Asp Ala Gln Thr Leu Arg Lys Ala Met Lys
 1               5                  10                  15

Gly Leu Gly Thr Asp Glu Asp Ala Ile Ile Ser Val Leu Ala Tyr Arg
                20                  25                  30

Asn Thr Ala Gln Arg Gln Glu Ile Arg Thr Ala Tyr Lys Ser Thr Ile
        35                  40                  45

Gly Arg Asp Leu Ile Asp Leu Lys Ser Glu Leu Ser Gly Asn Phe
 50                  55                  60

Glu Arg Val Ile Val Gly Met Met Thr Pro Ser
 65                  70                  75

<210> SEQ ID NO 5
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 5

Gly Phe Asp Pro Asn Gln Asp Ala Glu Ala Leu Arg Thr Ala Met Lys
 1               5                  10                  15

Gly Phe Gly Ser Asp Glu Glu Ala Ile Leu Asp Ile Thr Ser Arg
                20                  25                  30

Ser Asn Arg Gln Arg Gln Glu Val Cys Gln Ser Tyr Lys Ser Leu Tyr
        35                  40                  45

Gly Arg Asp Leu Ile Ala Asp Leu Lys Ser Glu Leu Thr Gly Lys Phe
 50                  55                  60

Glu Arg Leu Ile Val Gly Leu Met Arg Pro Ser
 65                  70                  75

<210> SEQ ID NO 6
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 6

Gly Phe Asn Pro Asp Ala Asp Ala Lys Ala Leu Arg Lys Ala Met Lys
 1               5                  10                  15

Gly Leu Gly Thr Asp Glu Asp Thr Ile Ile Asp Ile Ile Thr His Arg
                20                  25                  30
```

```
Ser Asn Val Gln Arg Gln Gln Ile Arg Gln Thr Phe Lys Ser His Phe
        35                  40                  45

Gly Arg Asp Leu Met Thr Asp Leu Lys Ser Glu Ile Ser Gly Asp Leu
    50                  55                  60

Glu Arg Leu Ile Leu Gly Leu Met Met Pro Ser
65                  70                  75

<210> SEQ ID NO 7
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 7

Pro Gly Asp Ala Ile Arg Asp Ala Glu Ile Leu Arg Lys Ala Met Lys
1               5                   10                  15

Gly Phe Gly Thr Asp Glu Gln Ala Ile Val Asp Val Val Ala Asn Arg
            20                  25                  30

Ser Asn Asp Gln Arg Gln Lys Ile Lys Ala Ala Phe Lys Thr Ser Tyr
        35                  40                  45

Gly Arg Asp Leu Ile Lys Asp Leu Lys Ser Glu Leu Ser Gly Asn Met
    50                  55                  60

Glu Arg Leu Ile Leu Ala Leu Phe Met Pro Ser
65                  70                  75

<210> SEQ ID NO 8
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 8

His Phe Asn Pro Asp Pro Asp Val Glu Thr Leu Arg Lys Ala Met Lys
1               5                   10                  15

Gly Ile Gly Thr Asn Glu Gln Ala Ile Ile Asp Val Leu Thr Lys Arg
            20                  25                  30

Ser Asn Thr Gln Arg Gln Thr Ile Ala Lys Ser Phe Lys Ala Gln Phe
        35                  40                  45

Gly Arg Asp Leu Thr Glu Asp Leu Lys Ser Glu Leu Ser Gly Lys Leu
    50                  55                  60

Glu Arg Leu Ile Val Ala Leu Met Tyr Pro Ser
65                  70                  75

<210> SEQ ID NO 9
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 9

Gly Phe Asp Pro Leu Arg Asp Ala Glu Val Leu Arg Lys Ala Met Lys
1               5                   10                  15

Gly Phe Gly Thr Asp Glu Gln Ala Ile Ile Asp Cys Leu Gly Ser Arg
            20                  25                  30
```

```
Ser Asn Lys Gln Arg Gln Gln Ile Leu Leu Ser Phe Lys Thr Ala Tyr
        35                  40                  45

Gly Arg Asp Leu Ile Lys Asp Leu Lys Ser Glu Leu Ser Gly Asn Phe
    50                  55                  60

Glu Lys Thr Ile Leu Ala Leu Met Lys Thr Ser
65                  70                  75

<210> SEQ ID NO 10
<211> LENGTH: 75
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 10

Gly Phe Asp Val Asp Arg Asp Ala Lys Lys Leu Arg Lys Ala Met Lys
1               5                   10                  15

Gly Met Gly Thr Asn Glu Ala Ala Ile Ile Glu Ile Leu Ser Gly Arg
            20                  25                  30

Thr Ser Asp Glu Arg Gln Gln Ile Lys Gln Lys Tyr Lys Ala Thr Tyr
        35                  40                  45

Gly Arg Glu Leu Glu Glu Asp Leu Lys Ser Glu Leu Ser Gly Asn Phe
    50                  55                  60

Glu Lys Thr Ala Leu Ala Leu Leu Asp Arg Ser
65                  70                  75

<210> SEQ ID NO 11
<211> LENGTH: 79
<212> TYPE: PRT
<213> ORGANISM: Artificial Sequence
<220> FEATURE:
<223> OTHER INFORMATION: Synthetic Peptide; sequence derived from human
      annexin
<220> FEATURE:
<221> NAME/KEY: MISC_FEATURE
<222> LOCATION: (22)..(22)
<223> OTHER INFORMATION: Xaa = Leu, Met or Trp
<220> FEATURE:
<221> NAME/KEY: MISC_FEATURE
<222> LOCATION: (34)..(34)
<223> OTHER INFORMATION: Xaa = Thr or Lys
<220> FEATURE:
<221> NAME/KEY: MISC_FEATURE
<222> LOCATION: (45)..(45)
<223> OTHER INFORMATION: Xaa = Ser or Lys
<220> FEATURE:
<221> NAME/KEY: MISC_FEATURE
<222> LOCATION: (48)..(48)
<223> OTHER INFORMATION: Xaa = Phe or Tyr
<220> FEATURE:
<221> NAME/KEY: MISC_FEATURE
<222> LOCATION: (50)..(50)
<223> OTHER INFORMATION: Xaa = Thr or Glu
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
```

```
<400> SEQUENCE: 11

Gly Ser Gly Cys Gly Phe Asp Glu Arg Ala Asp Val Glu Thr Leu Arg
1               5                   10                  15

Lys Ala Met Lys Gly Xaa Gly Thr Asp Glu Glu Ser Ile Leu Thr Leu
            20                  25                  30

Leu Xaa Ser Arg Ser Asn Ala Gln Arg Gln Glu Ile Xaa Ala Ala Xaa
        35                  40                  45

Lys Xaa Leu Phe Gly Arg Asp Leu Leu Asp Asp Leu Lys Ser Xaa Leu
    50                  55                  60

Thr Gly Lys Phe Xaa Lys Xaa Val Val Ala Leu Leu Lys Pro Ser
65                  70                  75

<210> SEQ ID NO 12
<211> LENGTH: 78
<212> TYPE: PRT
<213> ORGANISM: Artificial Sequence
<220> FEATURE:
<223> OTHER INFORMATION: Synthetic Peptide; sequence derived from human
      annexin

<400> SEQUENCE: 12

Gly Ser Pro Gly Phe Asp Glu Arg Ala Asp Val Glu Thr Leu Arg Lys
1               5                   10                  15

Ala Met Lys Gly Leu Gly Thr Asp Glu Glu Ser Ile Leu Thr Leu Leu
            20                  25                  30

Thr Ser Arg Ser Asn Ala Gln Arg Gln Glu Ile Ser Ala Ala Tyr Lys
        35                  40                  45

Thr Leu Phe Gly Arg Asp Leu Leu Asp Asp Leu Lys Ser Glu Leu Thr
    50                  55                  60

Gly Lys Phe Glu Lys Leu Val Val Ala Leu Leu Lys Pro Ser
65                  70                  75

<210> SEQ ID NO 13
<211> LENGTH: 83
<212> TYPE: PRT
<213> ORGANISM: Artificial Sequence
<220> FEATURE:
<223> OTHER INFORMATION: Synthetic Peptide; sequence derived from human
      annexin
<220> FEATURE:
<221> NAME/KEY: MISC_FEATURE
<222> LOCATION: (25)..(25)
<223> OTHER INFORMATION: Xaa = Leu, Met or Trp
<220> FEATURE:
<221> NAME/KEY: MISC_FEATURE
<222> LOCATION: (37)..(37)
<223> OTHER INFORMATION: Xaa = Thr or Lys
<220> FEATURE:
<221> NAME/KEY: MISC_FEATURE
<222> LOCATION: (48)..(48)
<223> OTHER INFORMATION: Xaa = Ser or Lys
<220> FEATURE:
<221> NAME/KEY: MISC_FEATURE
<222> LOCATION: (51)..(51)
<223> OTHER INFORMATION: Xaa = Phe or Tyr
<220> FEATURE:
<221> NAME/KEY: MISC_FEATURE
<222> LOCATION: (53)..(53)
<223> OTHER INFORMATION: Xaa = Thr or Glu
<220> FEATURE:
<221> NAME/KEY: MISC_FEATURE
<222> LOCATION: (66)..(66)
<223> OTHER INFORMATION: Xaa = Glu or Lys
<220> FEATURE:
<221> NAME/KEY: MISC_FEATURE
<222> LOCATION: (72)..(72)
<223> OTHER INFORMATION: Xaa = Glu or Lys
```

```
<220> FEATURE:
<221> NAME/KEY: MISC_FEATURE
<222> LOCATION: (74)..(74)
<223> OTHER INFORMATION: Xaa = Glu or Leu

<400> SEQUENCE: 13

Gly Ser Glu Cys Asp Phe Pro Gly Phe Asp Glu Arg Ala Asp Val Glu
1               5                   10                  15

Thr Leu Arg Lys Ala Met Lys Gly Xaa Gly Thr Asp Glu Glu Ser Ile
            20                  25                  30

Leu Thr Leu Leu Xaa Ser Arg Ser Asn Ala Gln Arg Gln Glu Ile Xaa
        35                  40                  45

Ala Ala Xaa Lys Xaa Leu Phe Gly Arg Asp Leu Leu Asp Asp Leu Lys
    50                  55                  60

Ser Xaa Leu Thr Gly Lys Phe Xaa Lys Xaa Val Val Ala Leu Leu Lys
65                  70                  75                  80

Pro Ser Arg

<210> SEQ ID NO 14
<211> LENGTH: 87
<212> TYPE: PRT
<213> ORGANISM: Artificial Sequence
<220> FEATURE:
<223> OTHER INFORMATION: Synthetic Peptide; sequence derived from human
      annexin
<220> FEATURE:
<221> NAME/KEY: MISC_FEATURE
<222> LOCATION: (29)..(29)
<223> OTHER INFORMATION: Xaa = Leu, Met or Trp
<220> FEATURE:
<221> NAME/KEY: MISC_FEATURE
<222> LOCATION: (41)..(41)
<223> OTHER INFORMATION: Xaa = Tyr or Lys
<220> FEATURE:
<221> NAME/KEY: MISC_FEATURE
<222> LOCATION: (52)..(52)
<223> OTHER INFORMATION: Xaa = Ser or Lys
<220> FEATURE:
<221> NAME/KEY: MISC_FEATURE
<222> LOCATION: (55)..(55)
<223> OTHER INFORMATION: Xaa = Phe or Tyr
<220> FEATURE:
<221> NAME/KEY: MISC_FEATURE
<222> LOCATION: (57)..(57)
<223> OTHER INFORMATION: Xaa = Thr or Glu
<220> FEATURE:
<221> NAME/KEY: MISC_FEATURE
<222> LOCATION: (70)..(70)
<223> OTHER INFORMATION: Xaa = Glu or Lys
<220> FEATURE:
<221> NAME/KEY: MISC_FEATURE
<222> LOCATION: (76)..(76)
<223> OTHER INFORMATION: Xaa = Glu or Lys
<220> FEATURE:
<221> NAME/KEY: MISC_FEATURE
<222> LOCATION: (78)..(78)
<223> OTHER INFORMATION: Xaa = Glu or Leu

<400> SEQUENCE: 14

Gly Ser Gly Cys Gly Thr Glu Thr Asp Phe Pro Gly Phe Asp Glu Arg
1               5                   10                  15

Ala Asp Val Glu Thr Leu Arg Lys Ala Met Lys Gly Xaa Gly Thr Asp
            20                  25                  30

Glu Glu Ser Ile Leu Thr Leu Leu Xaa Ser Arg Ser Asn Ala Gln Arg
        35                  40                  45

Gln Glu Ile Xaa Ala Ala Xaa Lys Xaa Leu Phe Gly Arg Asp Leu Leu
    50                  55                  60
```

```
Asp Asp Leu Lys Ser Xaa Leu Thr Gly Lys Phe Xaa Lys Xaa Val Val
65                  70                  75                  80

Ala Leu Leu Lys Pro Ser Arg
                85
```

<210> SEQ ID NO 15
<211> LENGTH: 75
<212> TYPE: PRT
<213> ORGANISM: Artificial Sequence
<220> FEATURE:
<223> OTHER INFORMATION: Synthetic Peptide; sequence derived from human annexin
<220> FEATURE:
<221> NAME/KEY: MISC_FEATURE
<222> LOCATION: (1)..(6)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (7)..(7)
<223> OTHER INFORMATION: Xaa = chosen, independently of the other amino acids of the sequence, from Asp and Glu
<220> FEATURE:
<221> NAME/KEY: MISC_FEATURE
<222> LOCATION: (8)..(8)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (9)..(10)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (11)..(11)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (13)..(14)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (15)..(15)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (18)..(18)
<223> OTHER INFORMATION: Xaa = chosen, independently of the other amino acids of the sequence, from Ala, Asn, Cys, Gln, Gly, His, Ile, Leu, Met, Phe, Ser, Thr, Trp, Tyr and Val,
<220> FEATURE:
<221> NAME/KEY: MISC_FEATURE
<222> LOCATION: (21)..(21)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (23)..(24)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr

```
<220> FEATURE:
<221> NAME/KEY: MISC_FEATURE
<222> LOCATION: (25)..(25)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (26)..(28)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (29)..(29)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (30)..(31)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (33)..(36)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (37)..(37)
<223> OTHER INFORMATION: Xaa = chosen, independently of the other
      amino acids of the sequence, from Arg, Ala, Cys, Gly, Ile, Leu,
      Met, Phe, Trp, Tyr and Val
<220> FEATURE:
<221> NAME/KEY: MISC_FEATURE
<222> LOCATION: (38)..(39)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (40)..(40)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (41)..(43)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (44)..(44)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (45)..(49)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (51)..(51)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
```

```
<220> FEATURE:
<221> NAME/KEY: MISC_FEATURE
<222> LOCATION: (52)..(52)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (53)..(54)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly,
      His, Lys, Orn, Pro, Ser, Thr and Tyr
<220> FEATURE:
<221> NAME/KEY: MISC_FEATURE
<222> LOCATION: (56)..(56)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (59)..(59)
<223> OTHER INFORMATION: Xaa = chosen from Glu, Asp, Lys or Arg
<220> FEATURE:
<221> NAME/KEY: MISC_FEATURE
<222> LOCATION: (61)..(64)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (65)..(65)
<223> OTHER INFORMATION: Xaa = chosen from Glu, Asp, Lys or Arg
<220> FEATURE:
<221> NAME/KEY: MISC_FEATURE
<222> LOCATION: (66)..(67)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (68)..(68)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (69)..(71)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (72)..(72)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (73)..(75)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr

<400> SEQUENCE: 15

Xaa Xaa Xaa Xaa Xaa Xaa Xaa Xaa Xaa Xaa Xaa Arg Xaa Xaa Xaa Lys
1               5                   10                  15

Gly Xaa Gly Thr Xaa Glu Xaa Xaa Xaa Xaa Xaa Xaa Xaa Xaa Xaa Arg
            20                  25                  30

Xaa Xaa Xaa Xaa Xaa Xaa Xaa Xaa Xaa Xaa Xaa Xaa Xaa Xaa Xaa
        35                  40                  45
```

-continued

```
Xaa Arg Xaa Xaa Xaa Xaa Asp Xaa Lys Ser Xaa Leu Xaa Xaa Xaa Xaa
    50                  55                  60
Xaa Xaa Xaa Xaa Xaa Xaa Xaa Xaa Xaa Xaa Xaa
65                  70                  75
```

<210> SEQ ID NO 16
<211> LENGTH: 78
<212> TYPE: PRT
<213> ORGANISM: Artificial Sequence
<220> FEATURE:
<223> OTHER INFORMATION: Synthetic Peptide; sequence derived from human annexin
<220> FEATURE:
<221> NAME/KEY: MISC_FEATURE
<222> LOCATION: (1)..(9)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (10)..(10)
<223> OTHER INFORMATION: Xaa = chosen, independently of the other amino acids of the sequence, from Asp and Glu
<220> FEATURE:
<221> NAME/KEY: MISC_FEATURE
<222> LOCATION: (11)..(11)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (12)..(13)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (14)..(14)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (16)..(17)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (18)..(18)
<223> OTHER INFORMATION: Xaa = chosen from Ala, Cys, Gly, Ile, Leu, Met, Phe, Trp, Tyr and Val
<220> FEATURE:
<221> NAME/KEY: MISC_FEATURE
<222> LOCATION: (21)..(21)
<223> OTHER INFORMATION: Xaa = chosen, independently of the other amino acids of the sequence, from Ala, Asn, Cys, Gln, Gly, His, Ile, Leu, Met, Phe, Ser, Thr, Trp, Tyr and Val
<220> FEATURE:
<221> NAME/KEY: MISC_FEATURE
<222> LOCATION: (24)..(24)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr
<220> FEATURE:
<221> NAME/KEY: MISC_FEATURE
<222> LOCATION: (26)..(27)
<223> OTHER INFORMATION: Xaa = chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr

```
<220> FEATURE:
<221> NAME/KEY: MISC_FEATURE
<222> LOCATION: (28)..(28)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (29)..(31)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (32)..(32)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (33)..(34)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (36)..(39)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (40)..(40)
<223> OTHER INFORMATION: Xaa = chosen, independently of the other
      amino acids of the sequence, from Arg, Ala, Cys, Gly, Ile, Leu,
      Met, Phe, Trp, Tyr and Val
<220> FEATURE:
<221> NAME/KEY: MISC_FEATURE
<222> LOCATION: (41)..(42)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (43)..(43)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (44)..(46)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (47)..(47)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (48)..(52)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (54)..(54)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
```

```
<220> FEATURE:
<221> NAME/KEY: MISC_FEATURE
<222> LOCATION: (55)..(55)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (56)..(57)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (59)..(59)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (62)..(62)
<223> OTHER INFORMATION: Xaa = chosen from Glu, Asp, Lys or Arg
<220> FEATURE:
<221> NAME/KEY: MISC_FEATURE
<222> LOCATION: (64)..(67)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (68)..(68)
<223> OTHER INFORMATION: Xaa = chosen from Glu, Asp, Lys or Arg
<220> FEATURE:
<221> NAME/KEY: MISC_FEATURE
<222> LOCATION: (69)..(70)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (71)..(71)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (72)..(74)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr
<220> FEATURE:
<221> NAME/KEY: MISC_FEATURE
<222> LOCATION: (75)..(75)
<223> OTHER INFORMATION: Xaa = chosen from Ala, Cys, Gly, Ile, Leu,
      Met, Phe, Trp, Tyr and Val
<220> FEATURE:
<221> NAME/KEY: MISC_FEATURE
<222> LOCATION: (76)..(78)
<223> OTHER INFORMATION: Xaa = chosen, independently of one another,
      from natural amino acids or derivatives thereof, such that at
      least 50% of them are polar residues chosen from Arg, Asn, Asp,
      Cys, Gln, Glu, Gly, His, Lys, Orn, Pro, Ser, Thr and Tyr

<400> SEQUENCE: 16

Xaa Xaa Xaa Xaa Xaa Xaa Xaa Xaa Xaa Xaa Xaa Xaa Xaa Xaa Arg Xaa
1               5                   10                  15

Xaa Xaa Lys Gly Xaa Gly Thr Xaa Glu Xaa Xaa Xaa Xaa Xaa Xaa Xaa
            20                  25                  30

Xaa Xaa Arg Xaa Xaa Xaa Xaa Xaa Xaa Xaa Xaa Xaa Xaa Xaa Xaa Xaa
            35                  40                  45
```

```
Xaa Xaa Xaa Xaa Arg Xaa Xaa Xaa Xaa Asp Xaa Lys Ser Xaa Leu Xaa
    50              55              60

Xaa Xaa Xaa Xaa Xaa Xaa Xaa Xaa Xaa Xaa Xaa Xaa Xaa
65                  70                  75

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide; sequence derived from
      human annexin

<400> SEQUENCE: 17

Gly Ser Gly Cys
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide; sequence derived from
      human annexin

<400> SEQUENCE: 18

Gly Cys Gly Ser
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide; sequence derived from
      human annexin

<400> SEQUENCE: 19

Gly Ser Gly Ser
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide; sequence derived from
      human annexin

<400> SEQUENCE: 20

Gly Cys Gly Cys
1
```

PEPTIDES WITH AFFINITY FOR A PHOSPHOLIPID AND USES

TECHNICAL FIELD

The present invention relates to a family of peptides with affinity for a phospholipid and also to various uses of this peptide, in particular in the pharmaceutical field.

In general, the peptides of the present invention are useful for the specific recognition of lipid molecules. They can be used for engineering and creating compounds that recognize and sequester the lipids, in particular negatively charged lipids, such as phosphatidylserines, phosphatidic and lysophosphatidic acids, phosphatidyl-glycerols, cardiolipins and sphingosine-1-phosphates.

The abovementioned lipids play an important role in particular in cell signalling and may be present at the outer surface of cell membranes and/or may circulate in the blood subsequent to very diverse pathological events.

Various cellular events result in the appearance of negatively charged lipids, and in particular phosphatidylserines (PS), at the outer surface of cells; these events can result either from a fortuitous or pathological alteration of the cell, or from a programmed cell event such as cell death or apoptosis. The appearance of PS at the outer surface of cells therefore constitutes an important "primary message" reflecting the existence of a dysfunction. In the case of the blood clotting process, the mechanism is well described: the alteration in the blood vessel endothelial cells, either for accidental reasons or for more complex pathological reasons, brings about the appearance of this PS message at the outer surface of the cells in contact with the blood environment. This message is immediately recognized by certain circulating proteins which then trigger a cascade of events resulting in the well known phenomenon of blood clotting.

The invention takes advantage of the property of the peptides that it provides of binding, in the presence or absence of calcium, to lipids and in particular to those which are negatively charged, for developing compounds that can be used as research, diagnostic and therapeutic tools in the field of lipid effector recognition and of the detection of apoptosis, of blood clotting disorders, of septic shock and acute inflammatory pathologies in particular.

As regards research and diagnosis, the peptides of the invention can, for example, be coupled to molecules for detection, for example to a fluorescent molecule, to one of the partners of the avidin-biotin system, to a radio element with a short life, to a paramagnetic compound, or to particles of gold or of dense compounds for electron microscopy. With these molecules for detection, it is possible, for example, to detect apoptotic cells or to recognize negatively charged membrane microdomains.

The peptides of the present invention can therefore be used for "in vitro" detection of pathologies involving the appearance of negative charges at the surface of cells and the release of microvesicules into the blood.

The peptides of the present invention can also be used for the in vivo detection and the imaging of apoptotic foci, of thrombotic zones and, in general, of any centre exposing negatively charged lipids, when these peptides are coupled, for example, to a radio element with a short lifetime (scintigraphic images acquired by Single Photon Emission Computed Tomography (SPECT) or by Positron Emission Tomography (PET)) or to any contrast compound such as a gadolinium complex for magnetic resonance imaging (MRI).

As regards therapy, in general, the peptides of the present invention can be used alone or coupled to a therapeutic molecule for preparing a medicinal product. Such a medicinal product can, for example, be used for targeting this molecule to zones exhibiting negative charges, such as tumours exhibiting foci of apoptotic cells or inflammatory tumours.

The peptides of the present invention can, for example, be coupled to molecules with a thrombolytic action, for preparing a medicinal product that can be used in the treatment and the prophylaxis of thrombosis, or for preparing a molecule covering all thrombogenic biomaterials. The peptides of the present invention can therefore be used for targeting thrombolytic molecules to the site of the thrombus or to thrombogenic zones.

In another example of application of the present invention, the peptides of the invention can be used alone or coupled to an anti-inflammatory molecule, for preparing a medicinal product that can be used, for example, in acute pathologies such as asthma, ulcerative colitis (UC), Crohn's disease, septic shock, collagen diseases and arthritis.

Other applications will become further apparent to those skilled in the art on reading the description which follows.

STATE OF THE ART

A family of proteins, called annexins, have been described in the prior art as exhibiting reversible functional anchoring to the cell membrane, regulated by the calcium concentration and the presence of anionic phospholipids. The annexins constitute a family of proteins expressed in very diverse tissues, both in animals and in plants. It appears that they are expressed neither in bacteria nor in yeast.

The structure of annexins comprises four domains of approximately 70 amino acids, or residues, which are very moderately homologous in terms of sequence but virtually identical in terms of topology.

In document WO 92/19279, J. Tait describes conjugates with affinity for phospholipids. He describes in particular the use of an annexin, in particular of annexin V, for producing an active conjugate that can be used as a thrombolytic agent.

Unfortunately, the compound described in that document and prepared from the whole annexin by means of a process of genetic recombination has many drawbacks, which are in particular a low yield and a high production cost. The major drawbacks are especially the fact that a fragile conjugate is obtained due to its complex topology resulting in irreversible unfolding. In addition, these molecules exhibit great toxicity for the kidney and the heart.

The present inventors have described, in application WO-A-00/20453, a first family of peptides that overcomes the abovementioned drawbacks and has affinity for phospholipids and improved stability.

DISCLOSURE OF THE INVENTION

The aim of the present invention is to provide a novel family of peptides with affinity for lipids, in particular for phospholipids, that is more specific and further improved with respect to the products of the prior art.

The peptides of the invention also have the advantages of being more chemically stable than the compounds of the prior art and of being able to be produced reproducibly, with a high yield and a very low production cost compared with the compounds of the prior art.

The peptides of the present invention are characterized in that they comprise the peptide sequence (I; SEQ ID NO: 15) below:

(I)
$J^1-J^2-J^3-J^4-J^5-J^6-Z^7-U^8-J^9-J^{10}-U^{11}-Arg-J^{13}-J^{14}-$ $U^{15}-Lys-Gly-X^{18}-Gly-Thr-J^{21}-Glu-J^{23}-J^{24}-U^{25}-J^{26}-$ $J^{27}-J^{28}-U^{29}-J^{30}-J^{31}-Arg-J^{33}-J^{34}-J^{35}-J^{36}-B^{37}-J^{38}-$ $J^{39}-U^{40}-J^{41}-J^{42}-J^{43}-U^{44}-J^{45}-J^{46}-J^{47}-J^{48}-J^{49}-Arg-$ $J^{51}-U^{52}-J^{53}-J^{54}-Asp-U^{56}-Lys-Ser-Z^{59}-Leu-J^{61}-J^{62}-$ $J^{63}-J^{64}-Z^{65}-J^{66}-J^{67}-U^{68}-J^{69}-J^{70}-J^{71}-U^{72}-J^{73}-J^{74}-$ $J^{75}$ in which J, Z, U, X and B represent amino acids such that:
the amino acids J are chosen, independently of one another, from natural amino acids or derivatives thereof, such that at least 50% of them are polar residues chosen from Arg, Asn, Asp, Cys, Gln, Glu, Gly, His, Lys, Orn, Pro, Ser, Thr and Tyr,
the amino acids U are chosen from Ala, Cys, Gly, Ile, Leu, Met, Phe, Trp, Tyr and Val,
the amino acid $X^{18}$ is chosen, independently of the other amino acids of the sequence, from Ala, Asn, Cys, Gln, Gly, His, Ile, Leu, Met, Phe, Ser, Thr, Trp, Tyr and Val,
the amino acid $B^{37}$ is chosen, independently of the other amino acids of the sequence, from Arg, Ala, Cys, Gly, Ile, Leu, Met, Phe, Trp, Tyr and Val,
the amino acid $Z^7$ is chosen, independently of the other amino acids of the sequence, from Asp and Glu,
the amino acids $Z^{59}$ and $Z^{65}$ are, independently, Glu, Asp, Lys or Arg, the superscripts of J, Z, U, X and B representing the position of these amino acids in said sequence.

The peptide sequence above folds up in space so as to adopt its tertiary conformation, which is the active form of the peptide.

Amino acids 12, 15, 16, 17, 19, 20, 22, 50, 55, 57, 58, 59, 60 and 65 are the amino acids, or residues, of the present invention that are directly or indirectly involved in the binding to lipids, i.e. they are involved either in the three-dimensional structure of the peptide so that it adopts its active conformation allowing recognition of a negatively charged lipid, or in the peptide recognition site.

The amino acids J are the surface amino acids, or residues, of this peptide when it is in its folded and active conformation. These residues are arranged spatially such that they are partially or completely exposed to the solvent. According to the present invention, these amino acids J may, for example, be chosen, independently of one another, from all the natural amino acid residues Ala, Arg, Asn, Asp, Cys, Gln, Glu, Gly, His, Ile, Leu, Lys, Met, Orn, Phe, Pro, Ser, Thr, Trp, Tyr and Val, and such that at least 50% of them are polar residues chosen from Arg, Asn, Asp, Cys, Gln, Glu, Gly, His, Lys, Orn, Pro, Ser and Thr. Examples are given in the sequence listing in the appendix.

The amino acids U are the core residues of this peptide. In the folded and active conformation of the peptide, they are spatially arranged close to one another and are not exposed to the solvent. They constitute the hydrophobic core of the protein. The compact assembly of the atoms of these residues plays a predominant role in the stability of the peptide in its active conformation. These residues can be chosen from the list of amino acids U described above. Various examples of combinations of core residues in the peptide of sequence (I) of the present invention are given in table (1) below:

TABLE 1

|  | $U^8$ | $U^{11}$ | $U^{15}$ | $U^{25}$ | $U^{29}$ | $B^{37}$ | $U^{40}$ | $U^{44}$ | $U^{52}$ | $U^{56}$ | $U^{68}$ | $U^{72}$ |
|---|---|---|---|---|---|---|---|---|---|---|---|---|
| Ex a) | Val | Leu | Met | Ile | Leu | Arg | Ile | Tyr | Leu | Leu | Val | Leu |
| Ex b) | Ala | Ile | Ile | Ile | Leu | Arg | Ile | Tyr | Leu | Leu | Ile | Leu |
| Ex c) | Ala | Ile | Ile | Ile | Leu | Arg | Ile | Tyr | Leu | Leu | Met | Val |
| Ex d) | Ala | Leu | Met | Leu | Leu | Arg | Ile | Tyr | Leu | Leu | Ile | Met |
| Ex e) | Ala | Leu | Met | Ile | Ile | Arg | Val | Tyr | Leu | Leu | Ile | Met |
| Ex f) | Ala | Leu | Met | Ile | Ile | Arg | Ile | Phe | Leu | Leu | Ile | Met |
| Ex g) | Ala | Leu | Met | Ile | Val | Arg | Ile | Phe | Leu | Leu | Ile | Phe |
| Ex h) | Val | Leu | Met | Ile | Leu | Arg | Ile | Phe | Leu | Leu | Ile | Met |
| Ex i) | Ala | Leu | Met | Ile | Leu | Arg | Ile | Phe | Leu | Leu | Ile | Met |
| Ex j) | Ala | Leu | Met | Ile | Leu | Arg | Ile | Tyr | Leu | Leu | Ala | Ala |
| Ex k) | Val | Leu | Met | Ile | Leu | Arg | Ile | Tyr | Leu | Leu | Val | Leu |
| Ex l) | Val | Leu | Met | Ile | Leu | Arg | Ile | Phe | Leu | Leu | Val | Leu |

(Ex = example)

The function of the residue $X^{18}$ is to maintain the structure of the Gly-X-Gly loop in the active form of the peptide, in particular where the residues $Z^{59}$ and $Z^{65}$ are Glu, to modulate the hydrophobic and lipophilic nature of this loop, and to optionally provide new specific interactions with phospholipids. This is the case, for example, of the residues Asn, Cys, Ser, Thr, Trp and Tyr.

The residues $Z^{59}$ and $Z^{65}$ may advantageously be lysine residues, the effect of which is to replace the calcium ion with the positively charged —$NH_3^+$ group of the lysine and to improve the affinity of the peptide for a negatively charged membrane.

The peptide (I) of the present invention, in its active form, comprises three sites for binding to a calcium ion where the calcium ion complexed with this site constitutes one of the ligands of a negatively charged phospholipid. The first of these sites, called principle site, involves residues 15, 18, 19 and 59 as calcium ligands. The second of these sites, called secondary site, involves residues 20 and 22 as calcium ligands. The third of these sites, which is a low-affinity secondary site, involves residues 57, 60 and 65 as calcium ligands.

The residues involved overall in the binding to phospholipids are residues 12, 15, 16, 19, 20, 22, 50, 55, 57, 58, 69, 60 and 65. This list includes residues involved in calcium binding, the phospholipids being calcium ligands.

These residues may, of course, be replaced with residues that carry out the same function with a view to the same result in accordance with the present invention.

By way of example, according to the invention, the peptide of formula (I) may advantageously be a peptide sequence chosen from the peptide sequences ID No. 1 to ID No. 10 in the appendix.

The sequence (I) represents the peptides of the present invention in their shortest functional form. It is clearly understood that this sequence may also comprise, linked to the N-terminal end and/or to the C-terminal end of the sequence (I), one or more amino acids, for example from 1 to 15 amino acids, in general from 1 to 10 amino acids. Most preferably, these additional amino acids barely modify the activity of the peptides, or not at all, or else improve them.

For example, a small sequence, referred to below as a functionalization sequence, may be useful in particular for attaching a label to the peptide, for attaching a molecule for treating diseases to the peptide and/or for attaching said peptide to a support. The length of this functionalization series will be adjusted according to it use. Of course, this sequence will preferably not interfere with the activity of the peptides of the present invention. Those skilled in the art will be able to readily adjust the length and the nature of this functionalization sequence according to the use that they will make of a peptide of the present invention.

Thus, according to a first particular embodiment of the present invention, the peptides of the present invention may comprise, for example at their N-terminal end, a functionalization sequence of three amino acids. This functionalization sequence makes it possible to directly attach a molecule for treating diseases to the peptide and/or to directly attach said peptide to a support. The peptides in accordance with this embodiment can be defined by the sequence (II; SEQ ID NO: 16) below:

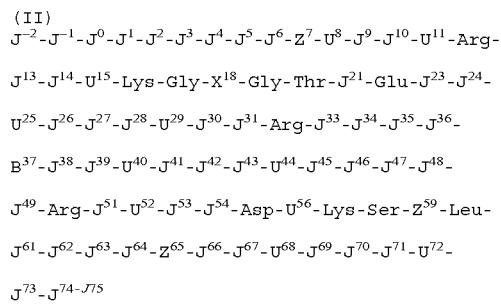

in which J, Z, U, X and B are as defined above.

For example, $J^{-2}$ may be Gly, $J^{-1}$ may be Ser, and $J^0$ may be Cys, Thr, Pro, Ser or Gln. This sequence $J^{-2}$-$J^{-1}$-$J^0$- may be chosen, for example, from Gly-Ser-Cys-, Gly-Ser-Thr-, Gly-Ser-Pro-, Gly-Ser-Ser-, Gly-Ser-Gly-, and Gly-Ser-Gln-. Thus, for example, each of the sequences ID No. 1 to ID No. 10 mentioned above may comprise, by choice, each one of the abovementioned functional sequences. The sequence ID No. 12 of the sequence listing in the appendix is only a nonlimiting example of a sequence (I) according to the present invention comprising, at its N-terminal end, a functional sequence of three amino acids.

According to a second particular embodiment of the present invention, the peptides of sequence (I) may comprise, for example, at their N-terminal end, a functionalization sequence of four amino acids $J^{-3}$-$J^{-2}$-$J^{-1}$-$J^0$-, chosen from Gly-Ser-Gly-Cys- (SEQ ID NO: 17), Gly-Cys-Gly-Ser- (SEQ ID NO: 18), Gly-Ser-Gly-Ser- (SEQ ID NO: 19), Gly-Cys-Gly-Cys- (SEQ ID NO: 20) and Gly-Cys-Gly-Ser- (SEQ ID NO: 18). This functionalization sequence is useful, for example, for direct attachment of a label such as technetium to the peptide. This embodiment is disclosed below. Thus, for example, each of the sequences ID No. 1 to ID No. 10 mentioned above may comprise, by choice, each one of the abovementioned functional sequences. The sequences ID No. 11 of the sequence listing in the appendix (several sequences are grouped together as a single one under the name ID No. 11) are merely nonlimiting examples of sequences (I) according to the present invention comprising, at their N-terminal end, a functional sequence of four amino acids.

According to a third particular embodiment of the present invention, the peptides of sequence (I) may comprise, for example at their N-terminal end, a functionalization sequence of seven to eleven amino acids. This functionalization sequence is useful, for example, for direct attachment of a label such as technetium to the peptide. This embodiment is disclosed below. Thus, for example, each of the sequences ID No. 1 to ID No. 10 mentioned above may comprise, by choice, each one of the abovementioned functional sequences. It is also possible to replace the sequence Gly-Ser-Gly-Cys (SEQ ID NO: 17) of the sequences ID No. 11 to 14 with Gly-Bb1-Gly-Bb2, in which Bb1 and Bb2 are, independently, Cys or Ser. These sequences ID No. 13 and 14 of the sequence listing in the appendix (several sequences are grouped together as a single one under the name ID No. 13 or 14) are merely nonlimiting examples of sequences (I) according to the present invention.

The peptides of the present invention have sufficient affinity for calcium and are capable of binding reversibly to lipid effectors, and in particular to those that are negatively charged, such as phosphatidylserines, phosphatidic acids, phosphatidylethanolamines, phosphatidylglycerols, cardiolipins and phosphatidylinositol phosphates.

It is a family of peptides, the main property of which is to specifically recognize the appearance of lipid signals at the surface of cell membranes in relation to the normal or pathological functioning of tissues.

The peptides of the present invention can be synthesized by the conventional synthetic processes of organic chemistry or of protein chemistry, and also by genetic recombination in vivo or in vitro, by genetic engineering, etc.

Thus, the present invention also relates to a process for producing a peptide according to the invention, said process comprising a solid-phase chemical synthesis of said peptide. The chemical synthesis can be carried out, for example, with an Applied Biosystems mod. 433A automatic peptide synthesizer. It can be carried out, for example, by Fmoc chemistry, which uses the fluorenylmethyloxycarbonyl group for temporary protection of the α-amino function of the amino acids.

The technical elements for carrying out this process of peptide synthesis are known to those skilled in the art. They are described, for example, in the book Solid-Phase Organic Synthesis by Kevin Burgess (Editor) Wiley-Interscience; ISBN: 0471318256; (February 2000).

The peptide of the invention may also be produced by genetic recombination in vivo, for example by means of a process comprising the following steps:

a) preparing a cDNA comprising a basic sequence encoding said peptide, b) inserting said cDNA into a suitable expression vector, c) transforming a suitable host cell with said vector into which the cDNA has been inserted, for replication of the plasmid, d) producing said peptide by translation of said cDNA in said host cell, and e) recovering the synthesized peptide.

According to the invention, the suitable expression vector and the host cell are chosen according to the usual techniques for genetic recombination. The vector may be any one of the plasmids generally used in this technique, for example a plasmid such as the vector pGEX-2T. Similarly, the cell may be chosen according to the usual techniques; it may, for example, be E. coli.

When an in vitro genetic recombination technique is used, steps c) and d) of the above process are replaced, respectively, with step c') for introducing the vector, into which the cDNA has been inserted, into a reaction medium that is suitable for replication of the plasmid, and step d') for producing said peptide by Translation of said cDNA in said suitable reaction medium. The document R. Jagus and G. S. Beckler (1998) Overview of eukaryotic in vitro translation and expression systems, *Current Protocols in Cell Biology* 11.1.1-11.1.13., 1989 by John Wiley & Sons, Inc., describes in vitro processes that can be used in the present invention.

The present invention also provides a chemical assembly with affinity for a phospholipid, comprising at least two peptides of the present invention, which may be identical or different, said peptides being linked to one another. These assemblies can be prepared, for example, by insertion of a flexible peptide linker, for example polyglycine, between the C-terminal residue of a peptide of the invention and the N-terminal residue of the second peptide, and so on according to the number of peptides placed end to end. This polyglycine linker may have the formula $-(Gly)_n-$, n being a integer ranging from 1 to 12, for example greater than 4. According to the invention, at least one of the peptides of the assembly can be a peptide comprising a sequence chosen from the sequences ID No. 1 to 10 of the sequence listing in the appendix.

These assemblies can also be synthesized by conventional synthetic processes of organic chemistry or of protein chemistry, and also by genetic recombination in vivo or in vitro, by genetic engineering, etc, for example by one of the abovementioned processes.

The aim of these assemblies is in particular to increase the affinity of the peptides of the present invention for the phospholipid, for example for a negatively charged phospholipid.

An assembly of the present invention can be used for three purposes: therapy, research and diagnosis, and there are a great many uses.

The pathologies especially targeted by the present invention are: (i) blood clotting disorders, (ii) apoptotic phenomena subsequent to the action of chemical compounds, of physical effects such as ionizing radiation, or of biological effects such as those linked to the formation or the necrosis of cancerous tissues, other than the normal phenomena of apoptosis, (iii) inflammatory pathologies, and (iv) disorders associated with the relationship between cells- and the extracellular matrix, and in particular collagen.

The peptides of the present invention also have a considerable advantage compared with the compounds of the prior art: the reversibility of their folding processes, which makes it possible to handle them at temperatures which are higher but compatible with the chemical stability of the peptides, for the purposes of chemical modifications with the aim of developing molecules that can be used in imaging and in therapeutics.

In addition, due to their small size, the peptides of the present invention can be readily combined with other proteins, either so as to form multifunctional chimeric proteins, or so as to introduce a mechanism of regulation by means of effectors other than the signalling phospholipids.

The peptides of the present invention can be used, as such, for producing a medicinal product that can be used for a treatment or for prophylaxis, since they have intrinsic anticoagulant and anti-inflammatory properties. They make it possible to effect a coating of cell surfaces, capable of prohibiting the access of compounds involved in the primary steps of blood clotting and inflammatory phenomena at these surfaces.

Thus, according to the invention, the peptides or assemblies of the present invention can be used, as such, for preparing a medicinal product, for example chosen from medicinal products intended for the treatment of a thrombosis, a medicinal product intended for the treatment of a tumour, and a medicinal product with anti-inflammatory action.

The peptides of the present invention can also be used, coupled to treatment molecules, for targeting these; molecules to areas exhibiting negative charges, such as a thrombus site or a site of inflammation or to an area of tumour. In this application, the peptides and assemblies of the present invention are, for example, coupled respectively to a molecule which has thrombolytic action, to a molecule which has anti-inflammatory action or to a molecule which has anti-tumour action. Examples of molecules with thrombolytic action that can be used according to the present invention are streptokinases, urokinases and plasminogen activators. In general, the peptides and assemblies of the present invention can be coupled, without distinction, to pro-apoptotic, anti-apoptotic and anti-inflammatory compounds.

The peptides and assemblies of the present invention can therefore be used, coupled to a molecule with thrombolytic activity, for producing a medicinal product that can be used in the treatment and the prophylaxis of thrombosis; coupled to a molecule with anti-inflammatory action, for producing a medicinal product that can be used, for example, locally or intravenously for treating acute pathologies such as asthma, UC, Crohn's disease, septic shock, collagen diseases and arthritis; or coupled to a molecule with anti-tumour action, for producing a medicinal product that can be used for treating tumours.

For use in research or diagnosis, the peptides of the present invention can be coupled to a labelling molecule for detection thereof. This labelling molecule may, for example, be a fluorescent molecule, particles of gold or of dense compounds, such as nanoparticles, for electron microscopy, a radio element, a paramagnetic compound and, in general, one of the labelling molecules commonly used in laboratories. To facilitate certain labelling or binding, this molecule may be linked to one of the partners of the avidin-biotin system.

According to the invention, the peptides and the chemical assemblies according to the invention can be coupled to a labelling molecule so as to form a labelling compound that can be used, for example, for in vivo or in vitro diagnosis.

In fact, the peptides of the present invention can be used for detecting pathologies involving the appearance of negative charges at the surface of cells and the release of microvesicules into the blood: for example, clotting disorders, acute inflammatory pathologies, etc., and apoptosis.

They can, for example, be coupled to radio elements with a short half-life, such as technetium or fluorine 18, and can allow "in vivo" detection of the location of thrombotic zones during vascular accidents of all sorts, in particular apoptotic and inflammatory foci, using imaging systems.

The peptides of the present invention can also, for example, be coupled to paramagnetic compounds, such as a gadolinium complex, to any contrast agents that can be used in magnetic resonance imaging (MRI), such as, for example, a paramagnetic compound or a ferromagnetic compound, or to any radio active element with a short life time. They can thus allow "in vivo" detection of the location of thrombotic zones, and apoptotic and inflammatory zones.

The abovementioned couplings can be carried out by any of the conventional techniques of organic chemistry known to those skilled in the art.

For example, in the case of technetium, the latter can be coupled directly to the peptide of the present invention, for example when the peptide of sequence (I) comprises a functionalization sequence such as those described above. This type of coupling is described, for example in document U.S. Pat. No. 6,323,313 by J. F. Tait et al. Those skilled in the art will understand that labels equivalent to technetium may also be coupled, in this way, directly to the peptides of the present invention.

Technetium, or any other metal such as those hereby mentioned, can also be coupled indirectly to the peptides of the present invention. This coupling is carried out, for example, by means of a cage that complexes said metal. This cage can be attached to the peptides of the present invention by means of a functionalization sequence such as those described above. In the example of technetium, technetium cages that can be used according to the present invention are described, for example, in the document 99 mTc Labeling of Highly Potent Small Peptides Shuang Liu, D. Scott Edwards, and John A. Barrett, *Bioconjugate. Chem.* 1997, 8, 621-636.

The peptides or assemblies that are coupled or ready to be coupled, according to the desired application, can be advantageously packaged in the form of diagnostic kits. Thus, the present invention also provides a diagnostic kit comprising a peptide or an assembly in accordance with the present invention. This diagnostic kit can, for example, also comprise a suitable reagent for detecting said labelling molecule.

The present invention also provides a kit for analysing and detecting negative charges at the surface of cells, characterized in that it comprises a peptide or a chemical assembly of the present invention, it being possible for the peptide or the assembly to be coupled to a label.

The present invention also provides a kit for analysing and detecting microvesicules in the blood, characterized in that it comprises a peptide or a chemical assembly in accordance with the present invention, it being possible for the peptide or the assembly to be coupled to a label.

In another application of the present invention, peptides or assemblies of the invention can be used, for example, for covering a biocompatible material. This type of material can be used in two types of conditions: i) extracorporeal circulations, and ii) blood storage.

Thus, the peptides of the present invention find an application for example, in the production of a filter for trapping and recovering, in extracorporeal blood circulation, activated circulating cells: platelets, red blood cells, leucocytes, etc. The blood reintroduced into the patient will thus be freed of the cells capable of creating abnormal coagulations, febrile reactions, etc. This filter can be in the form of a pleated film of biocompatible polymer onto which the peptides of the invention can be grafted by any appropriate means. These same filters can be introduced into the bags used to store the blood or can coat the inside of said bags. These filters constitute "sponges" capable of continuously capturing the blood cells containing the bags which are activated in particular subsequent to them ageing and to them undergoing the apoptotic process.

The various labellings, couplings and attachments disclosed above will be most preferably carried out while preserving the activity of the peptide of the present invention, in general at the ends or in the region of the ends of the peptides of the present invention or on surface residues.

Other advantages and characteristics of the present invention will become further apparent on reading the nonlimiting illustrative examples which follow, with reference to the figures in the appendix.

BRIEF DESCRIPTION OF THE SEQUENCE LISTING

The sequences ID No. 1 to ID No. 14 in the appendix are examples of peptides comprising the peptide sequence (I) and (II) of the present invention.

In particular, the sequences ID No. 11, ID No. 13 and ID No. 14 are examples of peptides comprising the peptide sequence of the present invention into which mutations have been introduced in order to increase the affinity for calcium and phospholipids.

BRIEF DESCRIPTION OF THE FIGURES

In FIG. 1, the upper and lower photographs represent various heart sections.

EXAMPLES

Example 1

Synthesis by Genetic Recombination: Expression and Purification of the Peptides of Sequences ID No. 1 to ID No. 12 of the Present Invention The sequences ID No. 1 to ID No. 14 were prepared by overexpression in *E. coli* according to the same protocol as that which was described by F. Cordier-Ochsenbein et al., in J. Mol. Biol. 279, 1177-1185.

Figure 2:
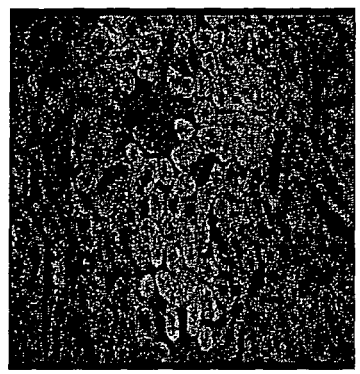
Figure 2:
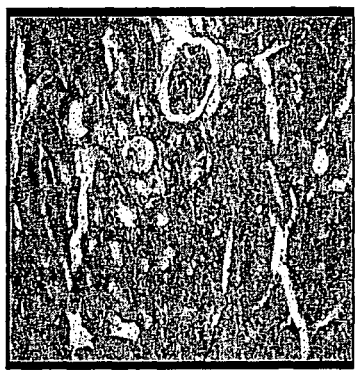
Figure 2:
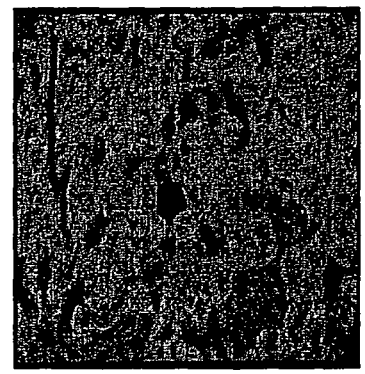
Figure 3:
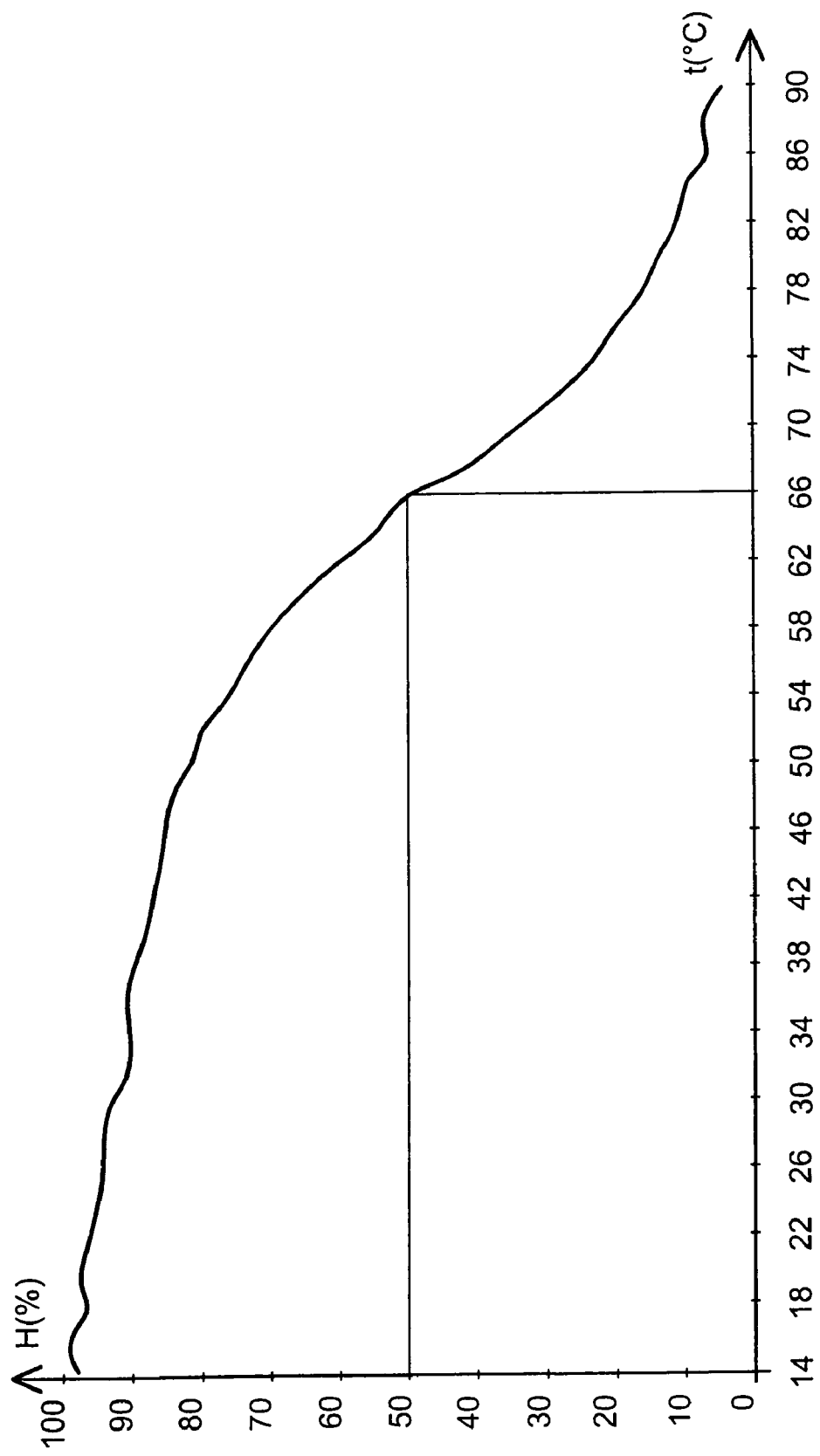
FIG. 3 is a graph which represents the degree of helicity "H" (as %) of a peptide according to the present invention as a function of the temperature "t" in ° C.

The cDNAs of each of these sequences were prepared using a polymerase chain reaction (PCR). They were inserted into the vector pGEX-2T (Smith & Johnson, 1998). FIG. 2 is a diagram illustrating the insertion of the cDNA into the vector. The absence of mutations induced by the PCR was verified by sequencing.

The production of the peptides is carried out using the *E. coli* strain BL21 containing the expression vector described above. After induction with isopropylthiogalactopyranoside (IPTG, 100 μm) up to an optical density of 1 at 600 nm, the growth is continued until a plateau is reached, i.e. for approximately 3 hours. After centrifugation, the bacteria are resuspended in the lysis buffer comprising 50 mM Tris-HCl, pH 8, 10 mM EDTA, 500 mM NaCl, 5% (v/v) glycerol, 1% (v/v) Triton X100, 1 mM dithiothreitol (DTT), 1 mM phenylmethylsulfonyl fluoride (PMSF) and 20 μg/ml of aprotinin.

The purification was carried out in the following way: after sonication and centrifugation at 10 000 g, the supernatant containing the soluble proteins is incubated with glutathione/agarose beads, allowing specific binding to these beads of the GST-domain fusion protein. After washing with a solution containing 1 M NaCl, 50 mM Tris-HCl, at pH 8, 70 units of thrombin per liter of culture are added and the sequences are eluted.

The sequences are then purified on a proRPC™ column of 16/10 type, provided by the company Pharmacia, using an FPLC system and at linear gradient of Millipore™ quality water containing 0.1% (v/v) of trifluoroacetic acid, TFA, and of acetonitrile containing 0.1% of TFA. The flow rate is adjusted to 2.5 ml/minute. Sequences are then lyophilized.

The final yield for each peptide is approximately 8 mg of sequence per liter of culture.

Example 2

Example of Chemical Synthesis of Peptides of the Present Invention

The peptides of the present invention were produced, in this example, by solid-phase chemical synthesis with an Applied Biosystems mod. 433A automatic peptide synthesizer, and with Fmoc chemistry, which uses the fluorenylmethyloxycarbonyl (Fmoc) group for temporary protection of the α-amino function of the amino acids.

The protective groups used to prevent the side reactions of the amino acid side chains, in this Fmoc strategy, were tert-butyl ether (tBu) for the Ser, Thr, and Tyr residues; tert-butyl ester (OtBu) for Asp and Glu; trityl (Trt) for Gln, Asn, Cys and His; tert-butyloxycarbonyl (Boc) for Lys; and 2,2,5,7,8-pentamethylchromane-6-sulphonyl (Pmc) for Arg.

The coupling reaction is carried out with an excess of 10 equivalents of amino acid (1 mmol) with respect to the resin (0.1 mmol). The protected amino acid is dissolved in 1 ml of N-methylpyrrolidone (NMP) and 1 ml of a 1 M solution of 1-N-hydroxy-7-azabenzotriazole (HOAt) in the solvent NMP. 1 ml of a 1 M solution of N,N'-dicyclohexylcarbodiimide (DCC) is then added. After activation for 40 to 50 minutes, the active ester formed is transferred into the reactor which contains the resin. Before the transfer and then coupling step, the resin is deprotected with respect to its Fmoc group with a 20% solution of piperidine in NMP. The excess piperidine is removed by washing with MNP after approximately 5 to 10 minutes.

During the deprotection, detection of the dibenzofulvene-piperidine adducts at 305 nm makes it possible to monitor the correct progress of the synthesis. In fact, quantification of the adduct makes it possible to estimate the effectiveness of the deprotection of the Fmoc group and, consequently, of the coupling of the last amino acid incorporated.

The cleavage of the resin and of the protective groups present on the side chains was carried out simultaneously by treatment of the peptide linked to the resin with trifluoroacetic acid. (TFA). Before carrying out the cleavage, the resin was washed several times with dichloromethane (DCM) and, finally, dried. The reactant used in the cleavage is an acid mixture containing 81.5% of TFA and triisopropylsilane (1%), ethanedithiol (2.5% when the peptide comprises a cysteine), water (5%) and phenol scavengers (5%). The resin was treated with this mixture for three hours with stirring and at ambient temperature, at a rate of 100 ml of solution per gram of resin. The free peptide in solution was recovered by filtration. The peptide was then precipitated and washed under cold conditions in diisopropyl ether, and then dissolved in 20% acetic acid and lyophilized.

The peptide recovered after lyophilization, the synthesis cruder is in reduced form, i.e. the interchain disulphide bridges are not formed.

The peptide is then purified on a proRPC™ column type 16/10, provided by the company Pharmacia, using an FPLC system and a linear gradient of Millipore™ quality water containing 0.1% by volume of trifluoroacetic acid TFA, and of acetonitrile containing 0.1% of TFA. The flow rate is adjusted to 2.5 ml/minute. The peptide is then lyophilized.

The products obtained were analysed by mass spectrometry.

Example 3

Stability of the Sequences ID No. 1 to ID No. 14

This example shows that the peptides of the present invention constitute stably folded proteins.

Composition of the Blank (Control):

50 mM Tris, 150 mM NaCl, 1 mM DTT, pH 8 10 μl $H_2O$ 990 μl

Adjusted to pH 8.

Composition of the Sample:

Sample: domain purified in 50 mM Tris buffer containing 150 mM NaCl, pH 8. Approx. concentration: 200 mg/ml.

Domain: 10 μl, i.e. final concentration of 300 μM.

$H_2O$: 990 μl.

pH measured at 7.8.

Hardware and Software Configuration:

Jobin Yvon CD6 device

CD-max software

Optical path of the measuring cuvette: 1 cm.

Figure 1:
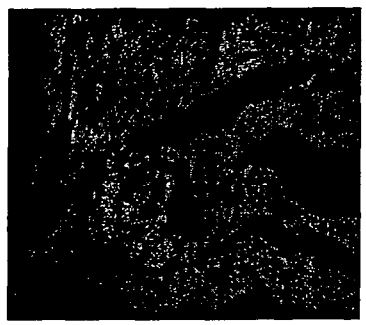
FIGS. 1 and 2 are micrographs obtained from tissue sections, respectively, of an apoptotic heart (FIG. 1) and of a kidney (FIG. 2). These sections were obtained, firstly (images on the left) with AFIM-fluorescein (AFIM-F) peptides of the present invention, secondly (images on the right) with annexin 5-fluorescein (A5-F) (compound of the prior art): fluorescence microscopy, magnification ×40. The images in the centre were obtained with haematoxylin: visible light microscope, magnification ×40.
Figure 1:
Figure 1:
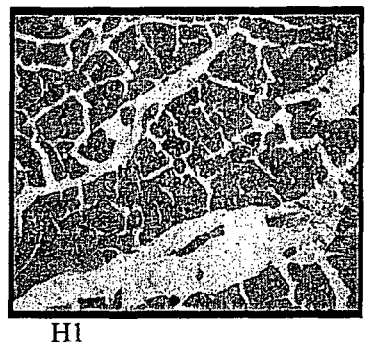
Figure 1:
Figure 1:
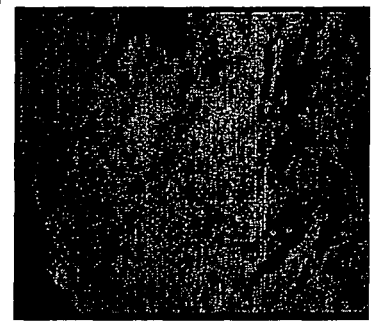

FIG. 1 in the appendix represents the degree of helicity of AFIM as a function of the temperature, as measured using the circular dichroisma signal in the far-UV at the wavelength of 200 nm.

In this figure, the value of the signal at 14° C. is taken for 100% of the helical content of the peptide. The thermal denaturation of the peptide is clearly cooperative and demonstrates that, at low temperature, and in particular at 37° C., it is a peptide that is suitably folded and exhibits improved stability.

Example 4

Assemblies of Two Peptides of the Present Invention

The process described in example 1 above is used to synthesize a peptide sequence of sequence ID No. 1-(Gly)$_4$—ID No. 1.

The final yield for the assembly is approximately 14 mg/liter of culture.

Example 5

Fluorescein Labelling of a Peptide of the Present Invention

In the examples which follow, the peptide of the present invention is called AFIM-SH. It has a peptide sequence as defined by the sequence (I). The sequences ID No. 1 to ID No. 14 are tested.

Fluorescein is a molecule which emits a green fluorescence with a wavelength of 525 nm when it is excited at a wavelength of 488 nm. The emission of green light is detected by cameras or photomultipliers. This coupling of AFIM to fluorescein makes it possible to detect the presence of cells exhibiting PS both in vitro and in vivo in small animals.

According to the present invention, it is possible to label AFIM on the surface residues, on any cysteine which would be introduced in place of any amino acid present at the surface of AFIM (surface residues) provided that the lipid membrane-binding function is not disturbed. AFIM thus modified is referred to as AFIM-SH below.

The coupling of the fluorescein is carried out by means of a maleimide function represented below on AFIM by the function SH.

The fluorescein is coupled to one or more cysteine(s) of the sequence, covalently, using a maleimide function.

General labelling scheme (Scheme I):

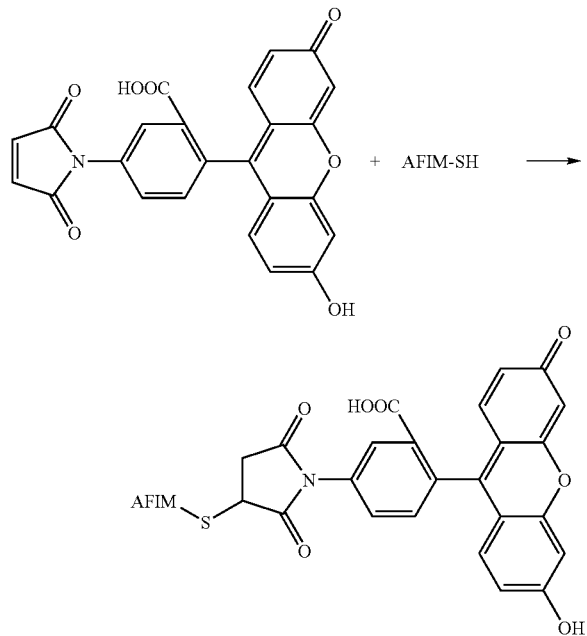

All the labelling is carried out at a temperature below 20° C.

AFIM-SH is in solution in Tris buffer (50 mM) containing NaCl (150 mM), pH=7.4. 5 equivalents of DTT in solution in the same buffer are added to the AFIM-SH solution. The medium is stirred for 30 min.

In the dark: fluorescein (5 equivalents of AFIM-SH+2 equivalents of DTT) is weighed out and dissolved in DMF, and added to the above solution. The entire mixture is stirred and the reaction is continued for 30 min. The medium is then diluted in 150 ml of PBS buffer (20 mM phosphate, 150 mM NaCl), pH=7.4, and ultrafiltered through a YM3 Membrane™. The sample is re-diluted and ultrafiltered several times, recording the UV spectrum of the filtrate.

When there is no more fluorescein in the filtrate (peak at 490 nm), the sample is concentrated to a few ml and stored chilled at 4° C.

The AFIM-fluorescein products were used to detect apoptotic cells by flow cytometry in vitro, and also in animals in vivo, in the manner described in example 6 below.

Example 6

Results of Labelling of Apoptotic Cells with the AFIM-Fluorescein Products

Imaging of apoptotic cardiac cells after infarction in rats.

A model of apoptosis in rats is used as described in the article published in *Circulation Res.* 1996, 79, 946-956.

Briefly, four rats (each weighing 300 g) were anaesthetized, intubated and ventilated. The myocardial ischemia was caused by temporary occlusion of the coronary artery. After occlusion for 30 minutes, the coronary artery was re-perfused for one hour.

At the end of the re-perfusion period, the AFIM-fluorescein peptides of example 5 were injected in the jugular vein at a rate of 200 µg of peptide for each of: two of the rats in the total volume of 1 ml.

By way of comparison, 200 µg of annexin 5-fluorescein (compounds of the prior art) were injected under the same conditions for each of the other two rats in a total volume of 1 ml.

The rats were sacrificed after 60 minutes.

Five organs were conserved for this study: the heart, the lung, the kidney, the liver and the brain. They were washed and rinsed in the presence of formol. The organs were then dehydrated and impregnated with paraffin for approximately 12 hours and then 7 µm sections were cut.

Some sections were stained with haematoxylin. The sections were examined under a fluorescence microscope and the adjacent sections stained with haematoxylin were examined with a visible light microscope. The haematoxylin-stained sections (marked H1 and H2 respectively on FIGS. 1 and 2 in the appendix) allow the architecture of the tissue to be visualized and the fluorescence microscopy makes it possible to detect the labelling with AFIM-fluorescein (AFIM-F) or with annexin 5-fluorescein (A5-F).

FIG. 1 in the appendix shows the images obtained for the apoptotic heart and FIG. 2 in the appendix shows the images obtained for the kidney.

FIG. 1 clearly shows the excess of fluorescein corresponding to the accumulation of label in the apoptotic cells. The contrast is visibly much better with AFIM of the present invention than with annexin 5 of the prior art.

FIG. 2 shows the labelling of the kidney associate with the partial elimination of the product. In the case of AFIM, the glomeruli do not appear to be labelled, only the proximal tubules are partially labelled. On the other hand, in the case of annexin 5 of the prior art, the entire renal tissue is strongly labelled, which is in agreement with the renal toxicity observed for this protein.

The results obtained in this example demonstrate a great specificity of the peptides of the present invention for cell labelling.

Labelling of the AFIM peptide, for example of ID No. 1 to 10, with fluorescein therefore makes it possible to effectively detect the phosphatidylserine (PS) present at the outer surface of cells involved in physiopathological processes such as programmed cell death (apoptosis), blood clotting or inflammatory reaction.

Example 7

Labelling of a Peptide of the Present Invention with Technetium $^{99m}$Tc

The labelling of AFIM with $^{99m}$Tc makes it possible, as for fluorescein, to detect phosphatidylserine (PS) present at the outer surface of cells involved in physiopathological processes such as programmed cell death (apoptosis), blood clotting or inflammatory reaction. $^{99m}$Tc is a γ-ray emitter which makes it possible to detect AFIM in any region of the body by means of various types of cameras that detect γ-radiation. This coupling of AFIM to $^{99m}$Tc makes it possible to detect the presence of cells exhibiting PS in vivo in any living being.

Two types of technetium labelling are disclosed in this example: indirect labelling (A) and direct labelling (B).

A) Indirect Labelling

In this example, AFIM-SH is coupled, at a cysteine in its sequence, to a complexing molecule, called cage molecule, capable of specifically receiving the $^{99m}$Tc ion. The coupling reaction is represented schematically below (Scheme II).

The cage molecule chosen is $NH_2$—$C_3(Bham)_2$ (2) described in the following document: Bis(Hydroxamamide)-Based Bifunctional Chelating Agent for $^{99m}$Tc Labelling of Polypeptides, Le-Cun Xu et al. *Bioconjugate Chem.* 1999, 10, 9-17. This cage is coupled to the maleimide derivative (1) according to Scheme (II) so as to give the label (3) which is then coupled to AFIM-SH so as to give the compound referred to as AFIM-cage (Scheme II)). The coupling is carried out in the following way:

AFIM-SH is in solution in Tris buffer (50 mM) containing NaCl (150 mM), pH=7.4. 5 equivalents of tris-(2-carboxyethyl)phosphine (TCEP) hydrochloride are weighed out dissolved in the same buffer, and added to AFIM-SH. The medium is stirred and left at ambient temperature for 3.0 minutes.

During this time, 10 equivalents of (1) are dissolved in dimethylformamide (DMF) and transferred onto 20 equivalents of cage (2) in the same volume of DMF. After reaction for 10 min, the product is added to AFIM-SH.

The entire mixture is stirred, and the reaction is continued at ambient temperature for 30 min. The medium is then dissolved in 150 ml of Tris buffer (50 mM) containing NaCl (150 ml), pH=7.4, and ultrafiltered through a YM3 Membrane™. The same is re-diluted and ultrafiltered several times, recording the UV spectrum of the filtrate. When there is no more DMF in the filtrate (peak at 214 nm), the sample is concentrated to a few ml and stored chilled (4° C.).

Scheme (II)

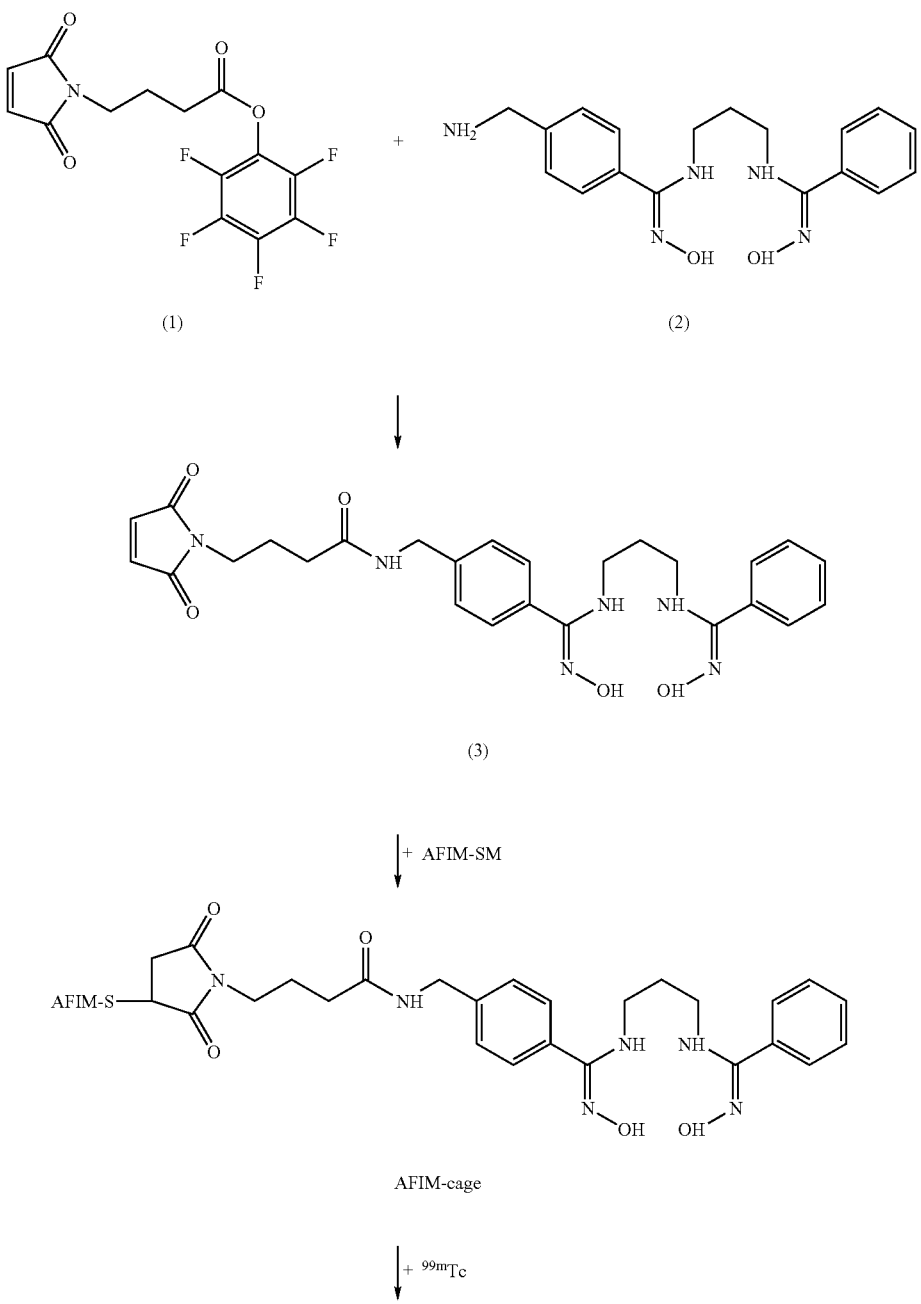

-continued

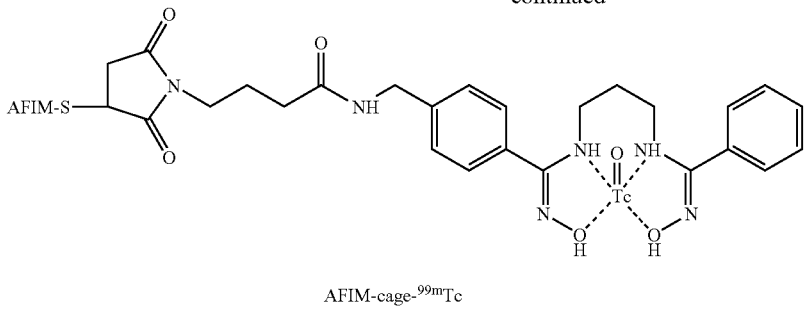

AFIM-cage-$^{99m}$Tc

An amount suitable for the size of the animal, of the peptide coupled to the technetium cage (AFIM-cage) prepared in this example, is taken and an aqueous solution of $SnCl_2$ (6 equivalents relative to the peptide) is added. The $^{99m}TcO_4^-$ solution is added and the reaction is continued for 30 minutes at ambient temperature.

The solution of labelled peptide (AFIM-cage-$^{99m}$Tc) is then directly injected intravenously into the animal.

The images are then collected by means of a camera capable of detecting γ-rays (SPECT or other camera).

B) Direct Labelling

In this example, AFIM is labelled with technetium without a cage. For this, AFIM is provided with a functionalization sequence of four amino acids which directly bind the technetium.

The peptide sequence ID No. 11 is used in this example. The functionalization sequence is Gly-Ser-Gly-Cys on the N-terminal side, residues 5 to 79 of the sequence ID No. 11 being those forming the sequence (I) of the present invention.

For the labelling, the peptide of sequence ID No, 11 and 5 equivalents of TCEP are dissolved in physiological saline and equilibrated for 15 min. 10 equivalents of $SnCl_2$ are then added. This solution can be lyophilized and stored under nitrogen.

The labelling is carried out by adding a solution of $^{99m}$Tc-$O_4^-$. After incubation for 15 minutes, the solution is passed over a PD10™ column.

The sequence ID No. 11 directly labelled with technetium (AFIM-$^{99m}$Tc) is injected intravenously.

The images are then collected with a camera such as those used above.

Example 8

Gadolinium Labelling of a Peptide of the Present Invention

AFIM coupled to gadolinium: AFIM-cage-Gd (indirect labelling)

The gadolinium labelling of AFIM makes it possible, as for the previous labels, to detect the phosphatidylserine (PS) present at the outer surface of cells involved in physiopathological processes such as programmed cell death (apoptosis), blood clotting or inflammatory reaction. Gadolinium is a paramagnetic agent which makes it possible to detect AFIM in any region of the body by means of nuclear magnetic resonance imaging processes. This coupling of AFIM to gadolinium makes it possible to detect, with a resolution which can range up to 1 mm, the presence of cells exhibiting PS in vivo in any living being.

As for fluorescein, AFIM can be coupled, at a cysteine, to a chemical molecule capable of specifically receiving the gadolinium ion. Once this gadolinium cage has been constructed, the coupling is carried out with AFIM as described below.

AFIM-SH is in solution in Tris buffer (50 mM) containing NaCl (150 mM), pH=7.4. 5 equivalents of TCEP are weighed out and dissolved in the same buffer, and added to AFIM-SH. The medium is stirred and left at ambient temperature for 30 min.

The gadolinium cage used is that described in the document P. KANTHI et al., "Synthesis of Charged and Uncharged Complexes of Gadolinium and Yttrium with Cyclic Polyazaphosphinic Acid Ligands for in vivo Applications", *J. CHEM SOC. PEKIN TRANS.* 2, 1993, pp. 605-618.

5 equivalents of cage, relative to AFIM-SH, are dissolved in DMF and added to AFIM-SH. The entire mixture is stirred, and the reaction is continued for 30 min at ambient temperature. The medium is then dissolved in 150 ml of Tris buffer (50 mM) containing NaCl (150 nM), pH=7.4, and ultrafiltered through a YM3 membrane. The sample is re-diluted and ultrafiltered several times, recording the UV spectrum of the filtrate. When there is no more DMF in the filtrate (peak at 214 nm), the sample is concentrated to a few ml and stored chilled at 4° C.

Once purified, the product is injected intravenously.

The images are collected by means of a detection camera.

Example 9

Gold Labelling of a Peptide of the Present Invention

The labelling of AFIM with gold is a direct labelling. It makes it possible to detect the phosphtidylserine (PS) present at the outer surface of the cells involved in physiopathological processes such as programmed cell death (apoptosis), blood clotting or inflammatory reaction.

Gold is an electron-dense metal, which means that it can be used in electron microscopy. This coupling of AFIM to gold makes it possible to detect and to locate the phosphatidylserine on a cellular and subcellular compartment scale. The coupled product can be used in vitro.

AFIM-SH is dissolved in Tris buffer (50 mM) containing NaCl (150 mM), pH=7.4. 5 equivalents of tris-(2-carboxyethyl)phosphine (TCEP) in solution in the same buffer are added to AFIM-SH. The medium is stirred for 15 min.

Modified gold beads (containing a grafted maleimide: Nanogold Monomaleimide Interchim™) are dissolved in 20

μl of DMSO and 200 μl of water, and added to the above solution (2 equivalents of beads relative to the protein).

The entire mixture is stirred, and the reaction is continued for one hour. The medium is then purified on a gel filtration column (Pharmacia PD-10™) and eluted with PBS buffer (20 mM phosphate, 150 mM NaCl), pH=7.4.

AFIM-Au can be used on tissue sections or on isolated cells. The analysis can be carried out by electron microscopy.

The invention claimed is:

1. A peptide consisting of a sequence selected from the sequences of SEQ ID No. 1 to SEQ ID No. 10.

2. The peptide according to claim 1, wherein a tripeptide sequence is further linked to the N-terminal end of the peptide, and said tripeptide sequence is selected from the group consisting of Gly-Ser-Cys-, Gly-Ser-Thr-, Gly-Ser-Pro-, Gly-Ser-Ser-, Gly-Ser-Gly-, and Gly-Ser-Gln-.

3. The peptide according to claim 1, wherein a tetrapeptide sequence is further linked to the N-terminal end of the peptide, and said tetrapeptide sequence is selected from the group consisting of Gly-Ser-Gly-Cys- (SEQ ID NO: 17), Gly-Cys-Gly-Ser- (SEQ ID NO: 18), Gly-Ser-Gly-Ser- (SEQ ID NO: 19), and Gly-Cys-Gly-Cys- (SEQ ID NO: 20).

4. A chemical assembly with affinity for a phospholipid, comprising at least two peptides as defined in claim 1, which may be identical or different, said peptides are linked to one another.

5. A labeling compound comprising a chemical assembly as defined in claim 4, coupled to a labeling molecule or to nanoparticles that are dense in electron microscopy, wherein the labeling molecule or the nanoparticles label the chemical assembly.

6. The labeling compound according to claim 5, in which the labeling molecule is a fluorescent molecule.

7. The labeling compound according to claim 5, in which the labeling molecule consists of one of the partners of the avidin-biotin system.

8. The labeling compound according to claim 5, in which the labeling molecule is a radio element.

9. The labeling compound according to claim 5, in which the labeling molecule is a contrast agent in magnetic resonance imaging.

10. The labeling compound according to claim 5, in which the labeling molecule is technetium.

11. The labeling compound according to claim 5, in which the nanoparticles that are dense in electron microscopy are gold nanoparticles.

12. A diagnostic kit comprising the labeling compound according to claim 5.

13. The diagnostic kit according to claim 12, also comprising a suitable reagent for detecting said labeling molecule.

14. A kit for analyzing and detecting microvesicules in the blood, comprising a chemical assembly according to claim 4.

15. The kit according to claim 14, in which the assembly is coupled to a label.

16. A kit for analyzing and detecting negative charges at the surface of cells, comprising a chemical assembly according to claim 4.

17. The kit according to claim 16, in which the assembly is coupled to a label.

18. A labeling compound comprising a peptide as defined in claim 1, coupled to a labeling molecule or to nanoparticles that are dense in electron microscopy.

19. The labeling compound according to claim 18, in which the labeling molecule is a fluorescent molecule.

20. The labeling compound according to claim 18, in which the labeling molecule consists of one of the partners of the avidin-biotin system.

21. The labeling compound according to claim 18, in which the labeling molecule is a radio element.

22. The labeling compound according to claim 18, in which the labeling molecule is a contrast agent in magnetic resonance imaging.

23. The labeling compound according to claim 18, in which the labeling molecule is technetium.

24. The labeling compound according to claim 18, in which the nanoparticles that are dense in electron microscopy are gold nanoparticles.

25. A diagnostic kit comprising a compound according to claim 18.

26. A diagnostic kit according to claim 25, also comprising a suitable reagent for detecting said labeling molecule.

27. A filter for dialyzing activated circulating blood cells, said filter comprises the peptide according to claim 1.

28. A kit for analyzing and detecting negative charges at the surface of cells, comprising a peptide according to claim 1.

29. The kit according to claim 28, in which the peptide is coupled to a label.

30. A kit for analyzing and detecting microvesicules in the blood, comprising a peptide according to claim 1.

31. The kit according to claim 30, in which the peptide is coupled to a label.

32. A peptide comprising the peptide according to claim 1 and a tripeptide sequence which is linked to the N-terminal end of the peptide according to claim 1, wherein said tripeptide sequence is selected from the group consisting of Gly-Ser-Cys-, Gly-Ser-Thr-, Gly-Ser-Pro-, Gly-Ser-Ser-, Gly-Ser-Gly-, and Gly-Ser-Gln-.

33. A filter for dialyzing activated circulating blood cells, said filter comprises the peptide according to claim 32.

34. A kit for analyzing and detecting negative charge at the surface of cells, comprising a peptide according to claim 32.

35. A chemical assembly with affinity for a phospholipid, comprising at least two peptides as defined in claim 32, which may be identical or different, said peptides being linked to one another.

36. A labeling compound comprising a chemical assembly as defined in claim 35, coupled to a labeling molecule or to nanoparticles that are dense in electron microscopy, wherein the labeling molecule or the nanoparticles label the chemical assembly.

37. The labeling compound according to claim 36, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

38. A kit for analyzing and detecting negative charge at the surface of cells, comprising a chemical assembly according to claim 35.

39. A labeling compound comprising a peptide as defined in claim 32, coupled to a labeling molecule or to nanoparticles that are dense in electron microscopy.

40. The labeling compound according to claim 39, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

41. A diagnostic kit comprising a compound according to claim 39.

42. A peptide comprising the peptide according to claim 1 and a tetrapeptide sequence which is linked to the N-terminal end of the peptide according to claim 1, wherein said tetrapeptide sequence is selected from the group consisting of Gly-Ser-Gly-Cys-, Gly-Cys-Gly-Ser-, Gly-Ser-Gly-Ser-, Gly-Cys-Gly-Cys- or Gly-Cys-Gly-Ser-.

43. A labeling compound comprising a peptide as defined in claim 42, coupled to a labeling molecule or to nanoparticles that are dense in electron microscopy.

44. The labeling compound according to claim 43, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

45. A diagnostic kit comprising a compound according to claim 43.

46. A chemical assembly with affinity for a phospholipid, comprising at least two peptides as defined in claim 42, which may be identical or different, said peptides being linked to one another.

47. A labeling compound comprising a chemical assembly as defined in claim 46, coupled to a labeling molecule or to nanoparticles that are dense in electron microscopy, wherein the labeling molecule or the nanoparticles label the chemical assembly.

48. The labeling compound according to claim 47, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

49. A kit for analyzing and detecting negative charge at the surface of cells, comprising a chemical assembly according to claim 46.

50. A filter for dialyzing activated circulating blood cells, said filter comprises the peptide according to claim 42.

51. A kit for analyzing and detecting negative charge at the surface of cells, comprising a peptide according to claim 42.

52. A peptide consisting of the sequence of SEQ ID No. 11, SEQ ID No. 12, SEQ ID No. 13, or SEQ ID No. 14.

53. A kit for analyzing and detecting negative charge at the surface of cells, comprising a peptide according to claim 52.

54. A filter for dialyzing activated circulating blood cells, said filter comprises the peptide according to claim 52.

55. A chemical assembly with affinity for a phospholipid, comprising at least two peptides as defined in claim 52, which may be identical or different, said peptides being linked to one another.

56. A labeling compound comprising a chemical assembly as defined in claim 55, coupled to a labeling molecule or to nanoparticles that are dense in electron microscopy, wherein the labeling molecule or the nanoparticles label the chemical assembly.

57. The labeling compound according to claim 56, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

58. A kit for analyzing and detecting negative charge at the surface of cells, comprising a chemical assembly according to claim 55.

59. A labeling compound comprising a peptide as defined in claim 52, coupled to a labeling molecule or to nanoparticles that are dense in electron microscopy.

60. The labeling compound according to claim 59, wherein the labeling molecule is selected from the group consisting of a fluorescent molecule, one of the partners of the avidin-biotin system, a radio element, a contrast agent in magnetic resonance imaging, and technetium, or wherein the nanoparticles that are dense in electron microscopy are gold nanoparticles.

61. A diagnostic kit comprising a compound according to claim 59.

* * * * *